United States Patent
Cho et al.

(10) Patent No.: US 6,638,272 B2
(45) Date of Patent: Oct. 28, 2003

(54) COOLING DELIVERY GUIDE ATTACHMENT FOR A LASER SCANNER APPARATUS

(75) Inventors: George Cho, Hopkinton, MA (US); Anthony P. Burns, Medway, MA (US)

(73) Assignee: Cynosure, Inc, Chelmsford, MA (US)

( * ) Notice: Subject to any disclaimer, the term of this patent is extended or adjusted under 35 U.S.C. 154(b) by 0 days.

(21) Appl. No.: 09/873,893

(22) Filed: Jun. 4, 2001

(65) Prior Publication Data

US 2002/0183732 A1 Dec. 5, 2002

(51) Int. Cl.$^7$ ................................................ A61B 18/18
(52) U.S. Cl. ............................. 606/13; 606/8; 606/10; 606/20; 606/22; 607/88; 607/91
(58) Field of Search ........................ 606/2, 8–10, 13, 606/16, 20, 22, 23; 607/88–91; 128/898

(56) References Cited

U.S. PATENT DOCUMENTS

| | | | | |
|---|---|---|---|---|
| 4,733,660 A | * | 3/1988 | Itzkan | 128/303.1 |
| 5,203,781 A | * | 4/1993 | Bonati et al. | 606/15 |
| 5,683,380 A | * | 11/1997 | Eckhouse et al. | 606/9 |
| 5,820,626 A | * | 10/1998 | Baumgardner | 606/13 |
| 5,830,208 A | * | 11/1998 | Muller | 606/9 |
| 6,059,820 A | * | 5/2000 | Baronov | 607/89 |
| 6,104,959 A | * | 8/2000 | Spertell | 607/101 |
| 6,235,015 B1 | * | 5/2001 | Mead, III et al. | 606/9 |
| 6,264,649 B1 | * | 7/2001 | Whitcroft et al. | 606/22 |
| 6,383,176 B1 | * | 5/2002 | Connors et al. | 606/9 |

* cited by examiner

Primary Examiner—Linda C. M. Dvorak
Assistant Examiner—Ahmed M Farah
(74) Attorney, Agent, or Firm—Don Halgren

(57) ABSTRACT

A delivery guide frame attachment for a laser scanner mechanism for a laser treatment operation, to permit proper spacing and dimensional stability of the laser scanner with respect to the skin of a patient being treated. The delivery guide frame attachment includes a housing having an upper end and a lower end. The lower end is applyable to the skin of a patient. The upper end is attached to the laser scanner. A chilled fluid supply conduit is arranged in communication with the housing for delivering a chilled fluid onto the skin of a patient when the housing is applied thereto. A chilled fluid containment arrangement in the housing retains and delays escape of chilled fluid from the housing placed on the patient, for a short period during the laser treatment operation.

4 Claims, 2 Drawing Sheets

COOLING DELIVERY GUIDE ATTACHMENT FOR A LASER SCANNER APPARATUS

BACKGROUND OF THE INVENTION

1. Field of the Invention

This invention relates to laser devices and more particularly to a frame attachment for a laser handpiece to provide proper framed spacing and cooling therewith.

2. Prior Art

The use of lasers for skin treatment is now a commonplace operation. Nonetheless, the use of the laser requires a skillful maneuvering of that apparatus on a patient being treated. Such skills include the ability to hold the laser device with dimensional stability with respect to the patient being treated. Improper laser firing for actuation upon the skin of a patient might result in burns.

In the use of a laser for hair reduction or removal, patient skin treatment also necessitates the cooling thereof for the comfort and proper treatment of the patient.

It is an object of the present invention, to provide a cooling handpiece attachment for use with a laser scanner for treatment of a patient's skin condition, which apparatus improves the prior art.

It is a further object of the present invention, to provide a cooling handpiece attachment with a scanner which permits dimensional stability in the use of a laser scanner apparatus with respect to the skin of a patient being treated.

It is a further object of the present invention to provide a cooling handpiece attachment for a scanner which maximizes the application of cooling fluid onto a patient's area being treated.

It is still yet a further object of the present invention to provide a cooling handpiece attachment which will facilitate the clean unhindered operation of the laser apparatus.

BRIEF SUMMARY OF THE INVENTION

The present invention relates to a delivery guide adaptor frame for a handheld laser scanner apparatus. The handheld laser scanner apparatus includes an optical fiber for conducting a laser beam from a laser to an optical scanner. The optical scanner receives the distal end of the optical fiber through the delivery guide and directs the laser beam through a scanner mechanism in the delivery guide or distance guide. The scanner mechanism controls the laser beam delivery on a patient's skin. The scanner may thus control the delivery of the output beam thereon. The scanner mechanism may include an electrical adapter cable for empowerment thereof. The scanner mechanism has a distalmost end through which the controlled laser beam is directed.

The delivery guide is connected to the distal end of the scanner mechanism and receives the laser beam through a scanner port arranged through a platform on the upper or proximal end of the delivery guide frame.

The delivery guide frame attachment (or housing) comprises a generally truncated housing having a proximal upper or first end which consists of the platform. The housing has a distal opened lowermost or second end which is applied to contact the patient's skin. The generally truncated housing is preferably of rectilinear configuration having a rear frame side, a first side, a forward side and a second side.

In a preferred embodiment, a cooling fluid port is angularly arranged on the rear frame side of the housing. The cooling fluid port has an uppermost end which receives a cooling fluid supply conduit thereon. The cooling fluid supply conduit is in fluid communication with a refrigeration unit or chiller for providing a supply of chilled fluid (ie. gas or liquid) and communicating that chilled fluid through the cooling fluid port and a cooling fluid discharge opening on the rear frame side of the housing. The cooling fluid is directed onto the surface of the patient being treated defined by the lower portion of the housing.

The first side wall of the housing has an elongated first-side portal disposed therein. The first side portal has an upper edge thereof which is in close proximity to the horizontal surface defined by the platform on the upper end of the housing. The first side portal has a lowermost edge which is spaced apart from the lowermost distal margin of the housing itself. The space between the lowermost edge of the first side portal and the lowermost edge or distal margin of the housing defines a skirt.

The housing has a forward-side wall with a forward portal disposed therethrough. The forward portal has an uppermost end which is further in distance from the platform of the housing than is the uppermost edge of the first side portal. The uppermost edge of the forward portal and the upper edge of the platform defines an enclosure panel for the "forward" containment of the debris generated by a laser treatment. The lowermost edge of the forward portal and the lowermost edge of the housing define a forward skirt portion of the housing arrangement, in a manner dimensionally similar to the skirt of the first side wall.

The second side wall of the housing arrangement preferably has a second side portal disposed therein in a manner geometrically and dimensionally similar to that of the first side portal in the first side wall. The second side portal has a lowermost edge which similarly defines a side skirt between the second side portal and the lowermost distal margin of the housing.

Initiating a skin treatment procedure, in operation of the laser apparatus and delivery guide (housing), the attending user would initiate laser action and control thereof by for example, a treadle or by an actuator switch on the scanner apparatus. The chilled "patient-treating" cooling fluid would be delivered through the cooling supply conduit and cooling fluid port and discharge opening onto the skin of a patient being treated after the housing was placed against the patient's skin.

The chilled cooling fluid reduces any pain associated with the particular laser treatment being performed thereon. Such laser treatment may for example, be hair removal or skin treatment or the like. The skirt portions on the first side, the second side and the forward side walls of the housing permits the chilled air being applied to the patient's skin to reside in that area being scanned by the laser apparatus. It "contains" the air within the treatment area, for a slightly longer period of time to help relieve the patient of any heat trauma.

The elongated first side portal and the elongated second side portal permit debris such as tissue or hair or the like to be discharged therethrough, without first contaminating and then damaging the lens of the scanner apparatus attached to the housing. The elongated forward portal in the forward wall of the housing is shorter than the adjacent first and second side portals, to provide space for the uppermost panel therein so as to promote side directionality and discharge of the debris during a laser and chilled-fluid blowing treatment procedure. The side discharge permits advancement of the housing and laser scanner apparatus over the patient and permits the attending physician a clearer view of the subject and the work site.

The invention thus comprises a delivery guide attachment frame for a laser scanner mechanism for a laser treatment operation, to permit proper spacing and dimensional stability of the laser scanner with respect to the skin of a patient being treated, the invention comprising a housing having an upper end and a lower end, the lower end being applyable to the skin of a patient, the upper end being attached to the laser scanner. A chilled fluid supply conduit is arranged in communication with the housing for delivering chilled fluid onto the skin of a patient when the housing is applied thereto. A chilled fluid containment arrangement in the housing retains and delays escape of chilled fluid on the patient for a short period during the laser treatment operation to increase the effective cooling thereby. The housing may be of generally rectilinear configuration, having a rearward frame wall, a forward wall and at least one side wall. The at least one side wall has a portal opening therein for discharge of debris and chilled fluid therefrom. The chilled fluid containment arrangement comprises a skirt disposed at a lower portion of the portal. The forward wall may have a portal opening therein. The portal in the side wall may have a higher upper end than the portal in the forward wall to create directionality of any discharge of debris from said housing. The rear frame wall may have an opening therein for receipt of the chilled fluid from the chilled fluid supply conduit. The upper end of said housing comprises a platform for communicable receipt of the scanner mechanism and a controlled laser light beam therethrough and onto a patient.

The invention also thus includes a method of providing dimension stability and cooling fluid discharge onto the skin site of a patient being treated by a laser beam, comprising the steps of: attaching an upper end of an elongated walled housing having a forward wall and a pair of side walls, to an energizable laser scanner; connecting a chilled fluid supply conduit to the housing; forming open portals in the forward and the side walls of the housing with a containment skirt adjacent a lower portion of the portals, energizing the laser and directing chilled fluid through the conduit to properly treat the patient; and blowing debris out the portals in the side walls. The steps may include the containing or slowing of the otherwise rapid escape of chilled fluid for a short period by the skirt about the lower end of the housing to provide comfort to the patient being treated. The portal in each of the side walls may be longer than the portal in the forward wall.

BRIEF DESCRIPTION OF THE DRAWINGS

The objects and advantages of the present invention will become more apparent, when viewed in conjunction with the following drawings in which.

DESCRIPTION OF THE PREFERRED EMBODIMENT

Figure 1:
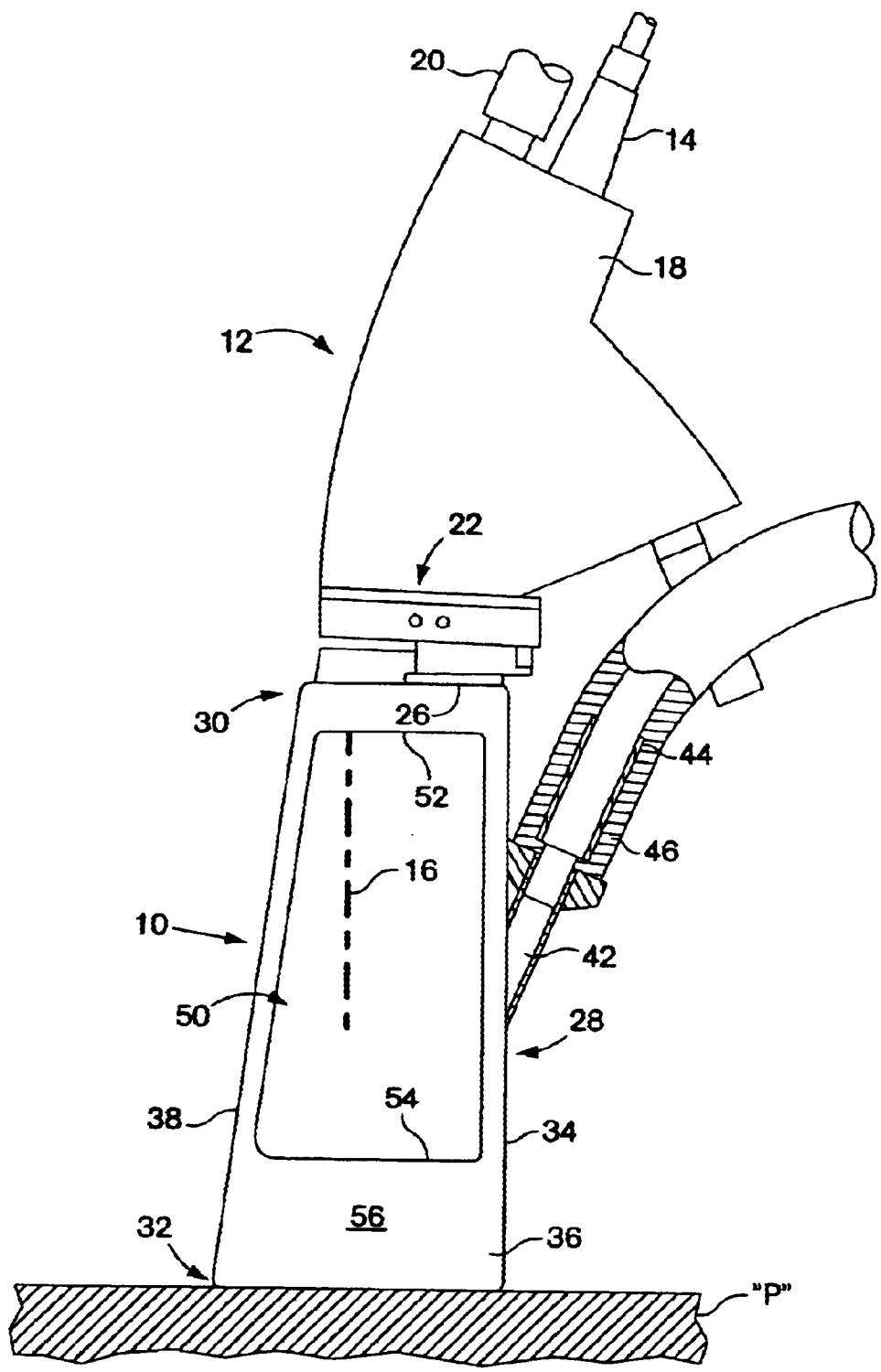
FIG. 1 is a side elevational view of a laser apparatus with a laser scanner attached to a delivery guide attachment for dimensional stability and cooling improvement of a patient's skin site during a laser treatment.

Referring now to the drawings in detail, and particularly to FIG. 1, there is shown the present invention which comprises a delivery guide 10 for a handheld optical laser scanner apparatus 12. The handheld laser scanner apparatus 12 includes an optical fiber 14 for conducting a laser beam 16 from a laser, not shown for clarity, to the optical scanner 12. The optical scanner 12 receives the distal end of the optical fiber 14 and directs the laser beam through a scanner mechanism within the scanner 12. The scanner mechanism controls the laser output display and direction onto the skin of a patient "P". The scanner mechanism may receive an electrical adapter cable 20 for empowerment thereof. The scanner 12 has a distalmost end 22 through which the controlled laser beam is directed.

Figure 2:
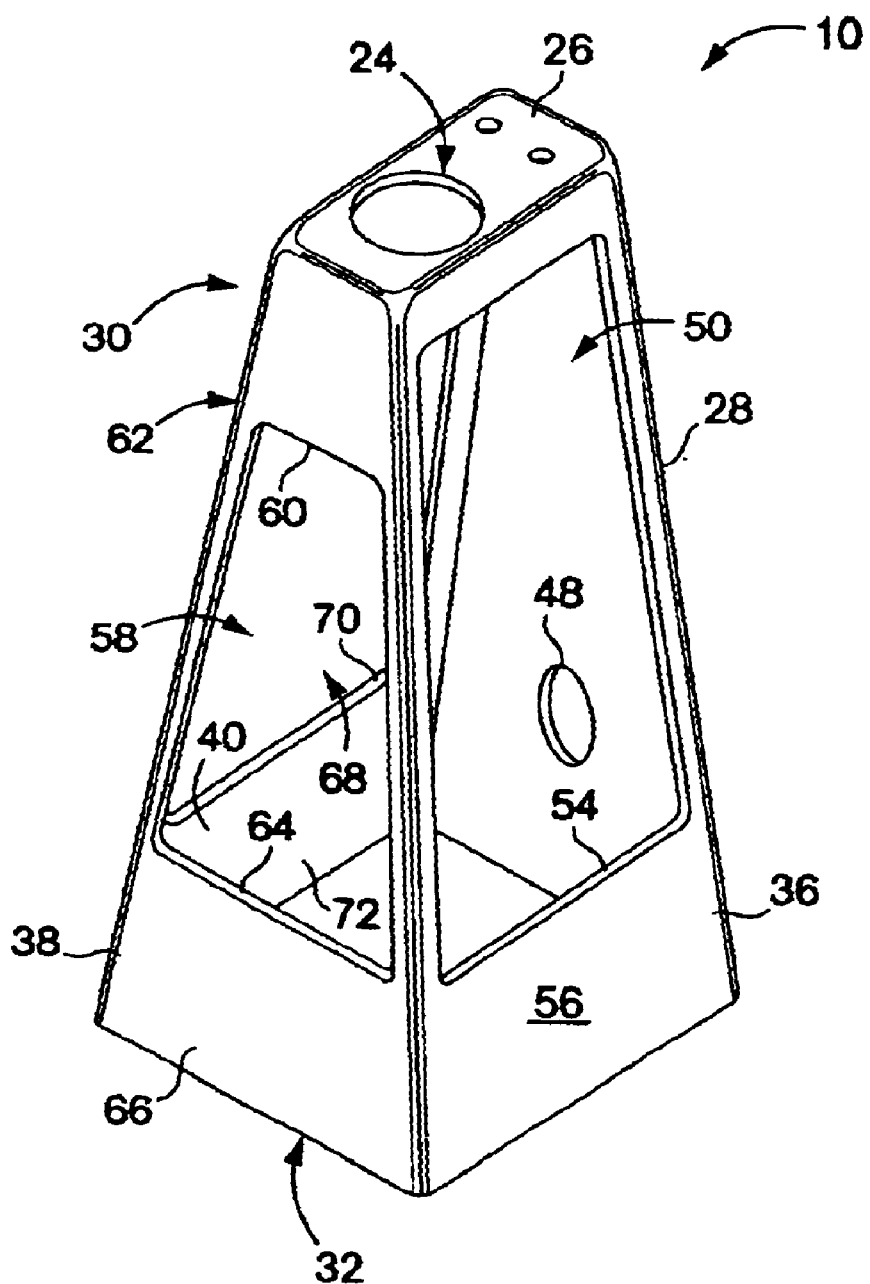
FIG. 2 a perspective view of the delivery guide housing shown in FIG. 1.

The delivery guide 10 is connected to the distal end of the scanner 12 and receives the laser beam through a scanner port 24 arranged through a platform 26 on the upper or proximal end of the delivery guide 10, as is shown in FIG. 2. The scanner port 24 may also include a lens mechanism, not shown for clarity, utilized to focus and/or protect the scanner mechanism housed within the optical scanner 12 itself.

The delivery guide or frame attachment 10, as shown in both FIGS. 1 and 2, comprises a generally truncated housing 28 having a proximal upper or first end 30 which consists of the platform 26. The housing 28 has a distal opened lowermost or second end 32 which is applied to contact the skin of the patient "P", as shown in FIG. 1. The generally truncated housing 28 is preferably of generally rectilinear configuration having a rear frame side 34, a first side 36, a forward side 38 and a second side 40.

A cooling fluid port 42 is angularly arranged on the rear frame side wall 34 of the housing 28, as shown in FIG. 1. The cooling fluid port 42 has an uppermost end 44 which receives a cooling fluid supply conduit 46 thereon. The cooling fluid supply conduit 46 is in fluid communication with a refrigeration and blower knit, not shown for clarity, for providing a supply of blown chilled fluid (for example, chilled gas or liquid) and communicating that chilled fluid through the cooling fluid port 42 and out a cooling fluid discharge opening 48 on the rear frame side wall 34 of the housing 28, as may be seen in FIG. 1. The cooling fluid is directed onto the surface area of the patient "P" being treated defined by the peripheral lower portion 32 of the housing 28.

The first side wall 36 of the housing 28 has an elongated first-side portal 50 disposed therein. The first side portal 50 has an upper edge 52 thereof which is in close proximity (for example, less than 2 cm.) to the horizontal surface defined as the platform 26 on the upper end 30 of the housing 28. The first side portal 50 has a lowermost edge 54 which is spaced apart from the lowermost distal peripheral margin 32 of the housing 28 (for example, by at least 2 cm.). The distance of at least about 2 cm. between the lowermost edge of the first side portal and the lowermost edge or distal margin 32 of the housing defines a skirt 56.

The forward-side wall 38 of the housing 28 has a forward portal 58 disposed therethrough. The forward portal 58 has an uppermost edge 60 which is further in distance from the platform 26 of the housing 28 than is the uppermost edge 52 of the first side portal 50, as may be seen in FIG. 1. The uppermost edge 60 of the forward portal 58 and the upper edge of the platform 26 defines an enclosure panel 62 (of at least 3 cm. in height) for the "forward" restrictive containment of the debris generated by a laser treatment during the blowing of chilled fluid through the opening 48. The lowermost edge 64 of the forward portal 58 and the lowermost edge 32 of the housing 28 defines a forward skirt portion 66 of the housing arrangement, in a manner dimensionally similar to the skirt 56 on the first side wall 36.

The second side wall 40 of the housing arrangement preferably has a second side portal 68 disposed therein in a manner geometrically and dimensionally similar to that of the first side portal 50 in the first side wall 36. The second side portal 68 has a lowermost edge 70 which similarly defines a side skirt 72 between the second side portal 68 and the lowermost distal margin 32 of the housing 28, as may be seen in FIG. 1.

During use of the laser scanner apparatus and the delivery guide 12 and 10, the user or attending physician would initiate laser action and control thereof by for example, a treadle or by an actuator switch, (not shown for clarity) on the scanner apparatus 12. The chilled "patient-treating" cooling fluid would be delivered through the cooling supply conduit 46 and cooling fluid port 42 and directed out the discharge opening 48 onto the skin of a patient "P" being treated after the housing was placed against the patient's skin.

The chilled cooling fluid is intended to reduce any pain associated with the particular laser treatment being performed thereon. Such laser scanned treatment may for example, be hair removal or skin treatment or the like. The skirt portions 56, 66 and 72 on the first side 36, the second side 40 and the forward side walls 38 of the housing 28 permits the chilled air being applied to the patient's skin, to "reside" in that area being scanned by the laser apparatus. It "contains" the air within the treatment area, for a slightly longer period of time to help maintain the coolness of the treated area and thus help relieve the patient of any heat trauma.

The elongated first side portal 50 and the elongated second side portal 68 permit debris such as tissue or hair or the like which may be loosened during the laser action and chilled fluid blowing thereon, to be discharged therethrough, without damaging the lens of the scanner apparatus 12 attached to the handpiece 10 or housing 28. The elongated forward portal 58 in the forward wall 38 of the housing 28 is shorter than the adjacent first and second side portals 50 and 68, to create the uppermost panel 62 therein so as to promote "side directionality" and "sideways directed" discharge of the debris during a laser and chilled-fluid blowing treatment procedure. The side discharge permits clearer advancement of the housing and laser apparatus 10 over the patient and permits the user physician a clearer view of the subject and the work site.

We claim:

1. A delivery guide attachment for a laser scanner mechanism for a laser treatment operation, to permit proper spacing and dimensional stability of said laser scanner with respect to the skin of a patient being treated comprising:

a housing having an upper end and a lower end, said lower end being applyable to the skin of a patient, said upper end being attached to said laser scanner;

a chilled fluid supply conduit arranged in communication with said housing for delivering chilled fluid onto the skin of a patient when said housing is applied thereto;

a chilled fluid containment arrangement in said housing to retain and delay escape of chilled fluid on said patient for a short period during said laser treatment operation;

wherein paid housing is of generally rectilinear configuration, having a rearward frame wall, a forward wall and at least one side wall, said at least one side wall has a portal opening therein for discharge of debris and chilled fluid therefrom, wherein said chilled fluid containment arrangement comprises a skirt disposed at a lower portion of said portal; and wherein said rear frame wall has an opening therein for receipt of said chilled fluid from said chilled fluid supply conduit wherein said forward wall has a portal opening therein; said portal in said side wall having a higher upper end than said portal in said forward wall to create directionality of any discharge of debris from said housing.

2. The delivery guide attachment as recited in claim 1 wherein said upper end of said housing comprises a platform for communicable receipt of said scanner mechanism and a laser light beam therethrough and onto a patient.

3. A method of providing dimension stability and cooling fluid discharge onto the skin site of a patient being treated by a laser beam, comprising the steps of:

attaching an upper end of an elongated walled housing having a forward wall and a pair of side walls, to an energizable laser scanner;

connecting a chilled fluid supply conduit to said housing;

forming open portals in both said forward and side walls of said housing with a containment skirt adjacent a lower portion of said portals;

energizing said laser and directing chilled fluid through said conduit to properly treat said patient; and blowing debris out said portals in said side walls wherein said portal in each of said side walls are longer than said portal in said forward wall to induce directionality to chilled fluid escaping from said housing.

4. The method as recited in claim 3, including the step of:

containing the escape of chilled fluid from said housing for a short period by said skirt about said lower end of said housing to provide comfort to the patient being treated.

* * * * *